(12) United States Patent
Heldmann et al.

(10) Patent No.: US 6,667,422 B2
(45) Date of Patent: Dec. 23, 2003

(54) PROCESS FOR THE PREPARATION OF α-HALOKETONES

(75) Inventors: Dieter Heldmann, Munich (DE); Juergen Stohrer, Pullach (DE)

(73) Assignee: Consortium fuer Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 10/233,925

(22) Filed: Sep. 3, 2002

(65) Prior Publication Data

US 2003/0060666 A1 Mar. 27, 2003

(30) Foreign Application Priority Data

Sep. 6, 2001 (DE) .......................... 101 43 742

(51) Int. Cl.⁷ .................. C07C 45/63; C07C 33/46; C07D 211/56; C07D 301/27
(52) U.S. Cl. ............ 568/319; 568/322; 568/323; 568/404; 568/407; 568/812; 568/814; 549/514; 549/520; 546/244; 546/245
(58) Field of Search .................. 568/319, 322, 568/323, 404, 407, 812, 814; 549/514, 520; 546/244, 245

(56) References Cited

U.S. PATENT DOCUMENTS

| | | |
|---|---|---|
| 5,481,011 A | 1/1996 | Chen et al. |
| 5,523,463 A | 6/1996 | Hilpert |
| 5,591,885 A | 1/1997 | Hilpert |
| 5,767,316 A | 6/1998 | Honda et al. |
| 5,902,887 A | 5/1999 | Honda et al. |
| 5,929,284 A | 7/1999 | Nishiyama et al. |

FOREIGN PATENT DOCUMENTS

| | | |
|---|---|---|
| EP | 0 774 453 A1 | 5/1997 |
| EP | 0 963 972 A2 | 12/1999 |

OTHER PUBLICATIONS

S.W. Kaldor et al., J. Med. Chem. 1997, 40, pp. 3979–3985.
P. Chen et al., Tetrahedron Letters 1997, 38 (18), pp. 3175–3178.
X. Wang et al., Synlett 2000, No. 6, pp. 902–904.
P.J. Kocienski, Protecting Groups, Thieme Veslag, 1994, Stuttgart, New York, pp. 185–243.
An English Abstract is enclosed for K.J. Schleifer, Pharmazie in unserer zeit 2000, 29, pp. 341–349.

Primary Examiner—Johann Richter
Assistant Examiner—Sikarl A. Witherspoon
(74) Attorney, Agent, or Firm—Brooks Kushman P.C.

(57) ABSTRACT

A process for preparing an α-haloketone of the formula (1)

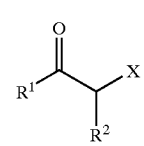

(1)

where $R^1$ is an optionally heteroatom-containing and optionally substituted hydrocarbon radical,
$R^2$ is a hydrogen, alkyl, aralkyl or aryl radical, and
X is a halogen radical,
by reacting a carboxylic acid derivative of the general formula (2)

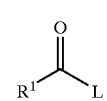

(2)

where L is a leaving group,
with a mono- or dienolate of a silyl ester of the formula (3)

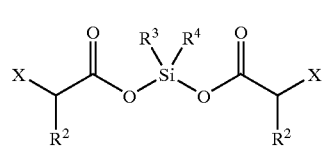

(3)

where $R^3$ and $R^4$ are identical or different alkyl, aryl, alkenyl or aralkyl radicals;
and hydrolyzing the reaction product immediately afterwards by adding acid and decarboxylating to (1). The product α-haloketone may be reduced to the corresponding α-haloalcohol.

14 Claims, No Drawings

PROCESS FOR THE PREPARATION OF α-HALOKETONES

BACKGROUND OF THE INVENTION

1. Field of the Invention

The invention relates to a process for preparing α-haloketones.

2. Background Art

The preparation of α-chloroketones by reacting an N-protected amino acid with alkyl chloroformates to give the mixed anhydride, reacting the mixed anhydride with diazomethane to give the diazoketone, and subsequently reacting the diazoketone with HCl to give the chloroketone is disclosed, for example, by S. W. Kaldor et al., J. Med. Chem. 1997, 40, 3979–3985. The process employs diazomethane, an explosive and carcinogenic gas which can only be used on the industrial scale at high risk. The preparation of α-chloroketones by reacting an N-protected amino ester with a $CH_2Cl$ anion at low temperatures is disclosed, for example, by P. Chen et al., TETRAHEDRON LETT. 1997, 38(18), 3175–3178, and by U.S. Pat. Nos. 5,481,011; 5,523,463; U.S. Pat. No. 5,591,885. The process must be carried out at very low temperatures (T<−−80° C.) which limits the general industrial utility and incurs significant cost disadvantages.

The preparation of α-chloroketones by reacting an N-protected amino ester with salts of chloroacetic acid and subsequent decarboxylation is disclosed, for example, by X. Wang et al., Synlett 2000, 902–904, and U.S. Pat. No. 5,929,284. For lithium salts, an industrial low temperature apparatus is again necessary. In the case of magnesium salts, the reaction may be carried out at or above room temperature, but the reaction then delivers only a 52% yield by chromatography.

The preparation of α-chloroketones by reacting an activated N-protected amino acid with alkali metal enolates of acetates to give β-ketoester derivatives which are then chlorinated selectively in the 2-position in a second step followed by decarboxylation in a third step is disclosed by EP 774 453 and U.S. Pat. Nos. 5,767,316 and 5,902,887. The three stage procedure is accordingly more costly and inconvenient than the previously described processes.

The preparation of α-chloroketones by reacting an activated N-protected amino acid with alkali metal enolates of monohaloacetates to give halogenated β-ketoester derivatives which are then hydrolyzed and decarboxylated in subsequent steps is described in U.S. Pat. Nos. 5,767,316 and 5,902,887. According to the inventors (EP 774 453 A1, page 5, lines 46–47), the process has to be carried out at −60° C. or lower which again requires an industrial low temperature facility.

SUMMARY OF THE INVENTION

It is an object of the present invention to provide an inexpensive process for preparing an α-haloketone from an N-protected amino acid derivative which may be carried out without risk on an industrial scale and which provides higher yields and purities than prior art processes. These and other objects are achieved by reacting a carboxylic acid derivative bearing a leaving group bonded to the carbonyl carbon, with a mono- or dienolate of a silyl ester.

DETAILED DESCRIPTION OF THE PREFERRED EMBODIMENT(S)

Thus, the subject invention is directed to a process for preparing an α-haloketone of the general formula (1)

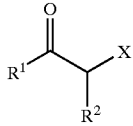

where $R^1$ is an alkyl, aralkyl or aryl radical in which $CH_2$ units may be replaced by heteroatoms such as NH, $NCH_3$, S or O, and CH units may be replaced by N, and the $R^1$ radicals may further be substituted by functional groups, for example a halogen radical, an amino radical, an alkoxy radical or a thioalkyl radical and
$R^2$ is a hydrogen, alkyl, aralkyl or aryl radical and
X is a halogen radical,
by reacting a carboxylic acid derivative of the general formula (2)

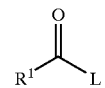

where $R^1$ is as defined above and
L is a leaving group,
with a mono- or dienolate of a silyl ester of the general formula (3)

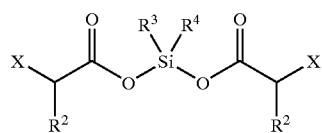

where X and $R^2$ are each as defined above, and $R^3$ and $R^4$ are identical or different and are each hydrogen, alkyl, aryl, alkenyl or aralkyl;
and hydrolyzing the reaction product immediately after the reaction and preferably without isolation, by adding acid and decarboxylating to (1).

The leaving group L is preferably a radical which increases the reactivity of a carboxylic acid derivative toward nucleophiles compared to the free carboxylic acid and supports substitution by these nucleophiles at the carbonyl carbon of the carboxylic acid derivative.

$R^1$ is preferably selected from the group of linear or branched alkyl radicals having from 1 to 25 carbon atoms, aryl radicals having from 6 to 30 carbon atoms and aralkyl radicals having from 7 to 31 carbon atoms, where the $CH_2$ units of each radical may be substituted by heteroatoms such as NH, $NCH_3$, S or O and the CH units by N, and the $R^1$ radicals may optionally be substituted by non-interfering functional groups including halogen radicals, amino radicals, alkoxy radicals, and thioalkyl radicals. Examples of $R^1$ include methyl, ethyl, propyl, butyl, pentyl, hexyl, heptyl, octyl, nonyl, isopropyl, isobutyl, t-butyl, 2,2-dimethylpropyl, 3-methylbutyl, phenyl, naphthyl and benzyl radicals.

The leaving group L is preferably selected from among alkoxy radicals having from 1 to 10 carbon atoms, optionally ring-substituted phenoxy or benzyloxy radicals, halogen radicals such as bromine or chlorine radicals, imidazolyl radicals, 1-oxybenzotriazole, and alkoxycarbonyloxy groups such as methoxycarbonyloxy, ethoxycarbonyloxy and isobutoxycarbonyloxy (mixed anhydrides). The leaving group L is preferably a linear alkoxy radical having from 1 to 4 carbon atoms, and is more preferably the methoxy radical.

X is Cl, Br, F or I, more preferably Cl or Br, most preferably Cl.

Preferably, the $R^2$ radicals are each independently hydrogen radicals, alkyl radicals having from 1 to 10 carbon atoms, aryl radicals having from 6 to 10 carbon atoms, aralkyl radicals having from 7 to 11 carbon atoms or alkenyl radicals having from 2 to 10 carbon atoms. A preferred $R^2$ radical is the hydrogen radical.

The $R^3$ and $R^4$ radicals are preferably each independently hydrogen radicals, alkyl radicals having from 1 to 10 carbon atoms, aryl radicals having from 6 to 10 carbon atoms or alkenyl radicals having from 2 to 10 carbon atoms. Examples of $SiR^3R^4$ silyl radicals include the dimethylsilyl, diethylsilyl, diisopropylsilyl, di-(t-butyl)silyl, dibutylsilyl, t-butylmethylsilyl, phenylmethylsilyl, diphenylsilyl and divinylsilyl radicals. Preferred silyl radicals are dimethylsilyl and diphenylsilyl radicals. A particularly preferred silyl radical is the dimethylsilyl radical.

Preference is given to carrying out the inventive process at a temperature in the range from –10° C. to 110° C., more preferably from 0° C. to 70° C. The process requires only one process step, requires no low temperature facility and no dangerous chemicals, employs inexpensive silyl radicals, and delivers better yields than the prior art processes.

Preference is given to carrying out the process in the presence of a solvent. In addition to aromatic hydrocarbons such as benzene, toluene or xylene, and aliphatic solvents such as hexane or heptane, preferred solvents include ethers such as t-butyl methyl ether, tetrahydrofuran, dioxane, diethyl ether, diisopropyl ether, dibutyl ether, and 1,2-dimethoxyethane.

It has surprisingly been discovered that silyl bis(α-halocarboxylate) esters can form stable enolates at room temperature or even at elevated temperature with selected bases, and that these enolates add onto activated (amino) acid derivatives in the desired manner and give the desired α-haloketones under acidic workup by immediate hydrolysis and in situ decarboxylation. In view of the prior art, it would have been expected that enolates of silyl haloacetates would only be suitable for preparing chloroketones at very low temperatures (T<–60° C.) and even then only in low yields of up to about 50%.

The present invention relates in particular to a process for preparing an α-haloketone of the general formula (5)

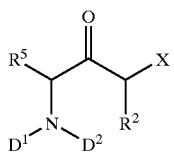

(5)

where $R^2$ is as defined above and $R^5$ is a hydrogen, alkyl, aralkyl or aryl radical in which one or more $CH_2$ groups may be replaced by O, S, NH or $NCH_3$, and X is a halogen radical and $D^1$ and $D^2$ are each independently a hydrogen radical or an amino protecting group, or are together a cyclic amino protecting group, by reacting an amino acid derivative of the general formula (6)

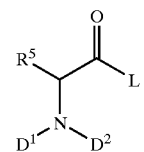

(6)

where $R^5$, $D^1$ and $D^2$ are each as defined above and L is a leaving group as defined above, with a metal enolate of a silyl ester of the general formula (3) and hydrolyzing the reaction product immediately afterwards by adding acid and decarboxylating to (5).

Preference is given to selecting $R^5$ from among hydrogen radicals, linear or branched alkyl radicals having from 1 to 20 carbon atoms where one or more $CH_2$ groups may be replaced by O, S, NH or $NCH_3$, aryl radicals having from 6 to 25 carbon atoms, aralkyl radicals having from 7 to 26 carbon atoms, optionally substituted vinyl and alkynyl radicals, and side chains of amino acids or of amino acid derivatives which are obtainable by chemical modification of the $R^1$ side chain of a natural or non-natural amino acid.

Examples of $R^5$ include hydrogen, methyl, ethyl, isopropyl, t-butyl, hydroxymethyl, chloromethyl, 1-hydroxyethyl, mercaptomethyl, methylthiomethyl, methylthioethyl, 2-methylpropyl, 1-methylpropyl, 1-hydroxyethyl, phenylthiomethyl, phenyl, benzyl, 2-phenylethyl, p-hydroxybenzyl, p-hydroxyphenyl, p-chlorophenyl, m-hydroxyphenyl, histidinyl, imidazolyl, triazolyl, tetrazolyl, 2-thiazolylthio, alkynyl, and vinyl radicals. Free hydroxyl, thiol or amino groups on the $R_5$ radicals may also be provided, if desired, with a protecting group by methods known to those skilled in the art, for example as disclosed in P. J. Kocienski, PROTECTING GROUPS, Thieme Verlag, 1994, Stuttgart, New York, pages 185–243. $R^5$ is more preferably a phenylthiomethyl or benzyl radical.

$D^1$ and $D^2$ are identical or different and are each preferably a hydrogen radical or amino protecting group. An amino protecting group is any protecting group which can be used for protecting amino functionality. Such protecting groups are well known Kocienski, id. Examples of such protecting groups include: methoxycarbonyl, ethoxycarbonyl, t-butoxycarbonyl (BOC), benzyloxycarbonyl (Z), fluorenyloxycarbonyl (FMOC), acetyl, benzyl, dibenzyl, phthalimido, tosyl, benzoyl, and silyl groups such as trimethylsilyl, stabase (2,2,5,5-tetramethyl-1-aza-2,5-disilacyclopentane derivatives) and benzostabase (2,2,5,5-tetramethyl-1-aza-2,5-disilabenzocyclopentane derivatives). The protecting group is preferably a t-butoxycarbonyl (BOC) or a benzyloxycarbonyl (Z) group.

The carboxylic acid derivative (6) is preferably an optically active, enantiomerically pure L- or D-amino ester. The optically active, enantiomerically pure L- or D-amino ester is preferably a compound from the group of tert-butoxycarbonyl- or benzyloxycarbonyl-protected L-phenylalanine esters or L-S-phenylcysteine esters.

The metal enolates of the silanes (3) are generated by reacting the silanes with two or more molar equivalents of bases, preferably in ether solvent, for example tetrahydrofuran or methyl tert-butyl ether.

Suitable bases for generating the enolate, which deprotonate either only one or both optionally $R^2$-substituted α-halocarboxylic acid moieties include all strong bases such as the alkali metal bases or alkaline earth metal bases. Useful bases include organolithium compounds, for example n-butyllithium, sec-butyllithium, tert-butyllithium, methyllithium, lithium diisopropylamide, lithium hexamethyldisilazide, lithium cyclohexylamide, and lithium cyclopentylamide; potassium tert-butoxide, sodium compounds such as sodium hydride, sodium methoxide, sodium ethoxide and the analogous potassium compounds; magnesium amides such as diisopropylamidomagnesium chloride, diisopropylamidomagnesium bromide, hexamethyldisilazidomagnesium chloride, hexamethyldisilazidomagnesium bromide, magnesium bis(diisopropylamide), magnesium bis(hexamethyldisilazide), cyclohexylamidomagnesium chloride, and cyclohexylamidomagnesium bromide and organomagnesium compounds such as tert-butylmagnesium chloride, n-butylmagnesium chloride, methylmagnesium chloride, t-amylmagnesium chloride and the corresponding bromides of these compounds; di-tert-butylmagnesium and diisopropylmagnesium. When organometallic compounds are used, an amine such as diisopropylamine, hexamethyldisilazane, triethylamine or diisopropylethylamine may also be added before or during the reaction. The molar ratio between the organometallic compound and amine is from 0.1 to 10. Preferred bases are magnesium compounds.

Particularly preferred bases are magnesium amides or a combination of an alkylmagnesium compound with an amine. Preference is given to preparing these bases by reacting a magnesium amide of the general formula (8)

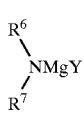

(8)

where
$R^6$ and $R^7$ are each independently alkyl, aralkyl, aryl, or silyl radicals, or $R^6$ and $R^7$ together are a cycloalkyl ring having from 4 to 6 carbon atoms, and
Y is —$NR^6R^7$ or a halogen radical;
or by reacting an organomagnesium compound of the formula (9)

 (9)

where
$R^8$ is an alkyl, aryl or aralkyl radical and
Z is a halogen radical or $R^3$,
or mixtures of compounds (9) as present in particular in Grignard solutions known as the Schlenk equilibrium, with a silyl ester of the general formula (3).

For the purposes of the present invention, the metal enolate refers in general to the active species which forms in the reaction between the silyl ester (3) and a strong base, i.e. a metal cation, for example Li or Mg, in a suitable solvent.

The term magnesium enolate refers to the active species which forms in the reaction between the silyl ester (3) and a magnesium base such as diisopropylamidomagnesium chloride in a suitable solvent which may deprotonate either only one or both optionally substituted α-halocarboxylic acid units.

Preferably, $R^6$ and $R^7$, independently, are linear or branched alkyl radicals having from 1 to 10 carbon atoms, aryl radicals having from 6 to 10 carbon atoms, aralkyl radicals having from 7 to 15 carbon atoms or silyl radicals having from 3 to 10 carbon atoms. Examples of $R^6$ and $R^7$ radicals include the methyl, ethyl, propyl, isopropyl, tert-butyl, phenyl, benzyl and trimethylsilyl radicals, or $R^6$ and $R^7$ together may be —$(CH_2)_4$— or —$(CH_2)_5$—. Particular preference is given to compounds where $R^6$ and $R^7$ are the same, and are isopropyl or trimethylsilyl radicals.

$R^8$ is preferably a linear or branched alkyl radical having from 1 to 10 carbon atoms, an aryl radical having from 6 to 10 carbon atoms or an aralkyl radical having from 7 to 15 carbon atoms. Examples of $R^8$ include methyl, ethyl, propyl, isopropyl, t-butyl, iso-butyl, n-butyl, phenyl or benzyl radicals. $R^8$ is more preferably a secondary or tertiary radical, for example an iso-propyl, sec-butyl or t-butyl radical.

Preference is given to carrying out the process of the invention in such a manner that a silyl ester (3) and a base of formula (8) or (9) and a carboxylic acid derivative of formula (2) or preferably an activated (amino) acid derivative of formula (6) are mixed together, preferably at from 0° C. to room temperature in one of the abovementioned solvents, and the solution is either stirred at room temperature until complete conversion or heated for 10–180 min at 40–110° C. On completion of the reaction, the solution which contains the addition product is admixed with dilute acid to liberate the product (1) or (5) in situ, and this mixture is extracted using a water-immiscible organic solvent, a haloketone-containing organic phase is removed, washed, preferably with a saturated $NaHCO_3$ or NaCl solution, and dried, preferably over $Na_2SO_4$ or $MgSO_4$. The solvent is then removed, the disiloxane formed is removed and the α-haloketone is obtained as a crystalline residue.

The molar ratio of base to silyl ester is preferably from 1 to 8, more preferably from 2 to 6. The molar ratio of the silyl ester to the carboxylic acid derivative is preferably from 0.5 to 2, more preferably from 0.5 to 1.5.

The reaction time at room temperature is preferably from 1 h to 16 h or, when heated, from 10 min to 3 h. It is preferable to conduct the reaction at a temperature of from 40 to 110° C., more preferably from 40 to 70° C., owing to the increased rate of reaction. Room temperature is preferably a temperature of from 20 to 25° C.

Reaction completion can be monitored by employing conventional techniques. When using diisopropylmagnesium chloride as base, completion may be recognized simply by clarification of the suspension to a solution. The workup procedure immediately following the actual reaction generally involves adding reaction batch slowly, for example dropwise, to dilute acid. In principle, only a pH in the range from acid to neutral is attained. Examples of usable acids include hydrochloric acid (i.e. from 2 to 30%) and sulfuric acid (i.e. from 2 to 20%) and the like, saturated ammonium chloride solution, or dilute acetic acid. On acidification, the product (1) or (5) is liberated in situ, since contact with water results in both the hydrolysis of the silyl ester immediately followed by decarboxylation to the haloketone.

After a neutral to acid pH of less than 7, preferably from 1 to 4, is attained and no more gas develops, the reaction mixture is extracted using a water-immiscible organic solvent. The water-immiscible organic solvent is preferably an acetic ester such as ethyl acetate, propyl acetate or butyl acetate, an ether such as t-butyl methyl ether, tetrahydrofuran, dioxane, diethyl ether, diisopropyl ether, dibutyl ether or 1,2-dimethoxyethane, or an aromatic hydrocarbon such as toluene, xylene or benzene. In principle, halogenated hydrocarbons such as dichloromethane or chloroform are also suitable, however, their higher densities may exacerbate problems associated with phase separation, requiring more extractant to be used. Following extraction, the haloketone-containing organic phase is preferably washed with saturated $NaHCO_3$ and/or NaCl solution and preferably dried, for example, over $Na_2SO_4$ or $MgSO_4$. After filtering off the drying agent and removing the solvent, the oligo- or polysiloxane formed is removed by stirring with petroleum ether.

The solid residue of α-haloketone may be used directly or after recrystallization. Particularly useful solvents for recrystallization include alcohols such as ethanol, 2-propanol, 2-butanol, hexanol and 2-ethylhexanol. These may also be used as mixtures with petroleum ether. Recrystallization also removes the co-produced siloxane —[Si(CH$_3$)$_2$O]—, so that stirring with petroleum ether may be omitted.

The crude or recrystalized α-haloketone may be reduced to form the corresponding α-haloalcohol. Reduction to the α-haloalcohol may take place by reduction of the α-haloketone using NaBH$_4$ under the conditions described by S. W. Kaldor et al., J. MED. CHEM. 1997, 40, 3979–3985, or, owing to the marked diastereoselectivity, most advantageously by Meerwein-Ponndorf-Verley (MPV) reduction as described, for example, in EP 963972, page 13, line 42 to page 14, line 11.

The following reaction scheme serves as a non-limiting example for the possible combinations of substrates and reagents of the present invention:

from (N-protected amino) acid derivatives. Starting from L-phenylalanine and L-phenylcysteine, reduction of the keto group gives the corresponding haloalcohols which can be further reacted to give HIV protease inhibitors (S. W. Kaldor et al., J. Med. Chem. 1997, 40, 3979–3985; K.-J. Schleifer, Pharmazie in unserer Zeit 2000, 29, 341–349).

In addition, purification may be effected by simple recrystallization. Column chromatography, which cannot be carried out on an industrial scale, is unnecessary.

The following examples serve to illustrate the invention:

EXAMPLE 1

Sodium chloroacetate (233 g, 2.00 mol) is suspended in absolute diethyl ether (400 ml). Dichlorodimethylsilane (122 ml, 1.00 mol) is added dropwise with stirring. To complete the reaction, the reaction mixture is heated for 60 minutes under reflux. After cooling, the NaCl formed is filtered off under an insert atmosphere. The crude product, which is obtained quantitatively, is isolated by evaporation of the ether and is sufficiently pure for the reaction described

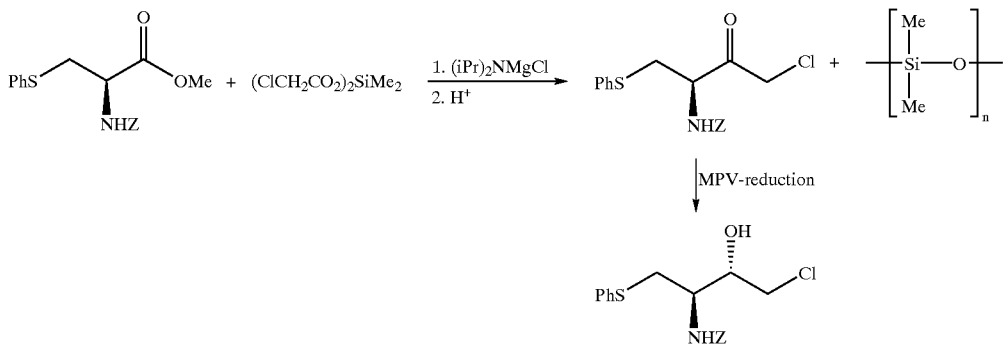
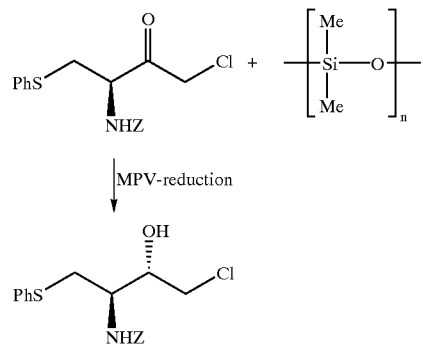

The present invention therefore also encompasses the preparation of an α-haloalcohol of the general formula (4)

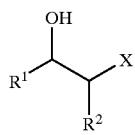

(4)

where R$^1$, R$^2$ and X are each as defined above by preparing an α-haloketone (1) by the process according to the invention and reducing the carbonyl group to the α-haloalcohol (4).

The invention also encompasses in particular the preparation of an α-haloalcohol of the general formula (7)

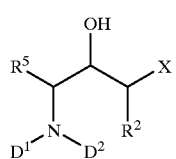

(7)

where R$^2$, R$^5$, D$^1$, D$^2$ and X are each as defined above, by preparing an α-haloketone (5) by the process according to the invention and reducing the carbonyl group to the α-haloalcohol (7).

The process according to the invention allows advantageous, inexpensive access to α-haloketones starting below. The crude product may be further purified for analytical purposes by fractional distillation. Colorless liquid (164 g, 67% after purification), b.p. 90° C./1 mbar. $^1$H NMR (CDCl$_3$): 0.50 (s, 6H), 4.08 (s, 4H). $^{29}$Si NMR: 8.88 ppm.

EXAMPLE 2

Diisopropylamine (21 ml, 150 mmol) is added dropwise at room temperature to methylmagnesium chloride (58 ml, 20% in tetrahydrofuran (THF), 150 mmol) with stirring, the suspension is diluted using absolute THF (30 ml), and heated for 60 min to reflux (flask 1). In a second flask, methyl N-Z-L-S-phenylcysteinate (8.6 g, 25 mmol) and bis(chloroacetoxy)dimethylsilane (6.1 g, 25 mmol) are dissolved in absolute THF (40 ml) with stirring at room temperature (flask 2). The suspension from the first flask is then added dropwise within 5 minutes to the solution in flask 2, resulting in a strongly exothermic reaction and formation of a yellow suspension. The mixture is kept under reflux for a further 45 min. During this time, the suspension becomes a clear solution. The reaction mixture is diluted using THF (100 ml), added dropwise to dilute sulfuric acid (10%), and washed with demineralized or distilled water and saturated NaCl solution. The organic phase is concentrated on a rotary evaporator. The residue crystallizes rapidly and is stirred with petroleum ether. The light beige crystals are filtered off with suction and dried in a drying cabinet. Yield 6.8 g (74%). Recrystallization from 2-propanol. m.p. 90–91° C. $^1$H NMR (CDCl$_3$): 3.22–3.45 (m, 2H), 4.10–4.25 (m, 2H), 4.63–4.75 (m, 2H), 5.10 (s, 2H), 5.50–5.65 (m, 1H), 7.15–7.45 (m, 10H). As an alternative workup, concentration of the solution and direct addition of isopropanol gives the product in crystalline form directly from the reaction mixture in a nonoptimized yield of 5.1 g (56%).

EXAMPLE 3

Methylmagnesium chloride solution (20% in THF, 300 mmol, 116 ml) was initially charged, heated to boiling and admixed dropwise with diisopropylamine (300 mmol, 42.0 ml). After the addition, the mixture was refluxed for a further 1 h, then cooled.

Methyl N-Z-L-phenylalaninate (37.5 mmol, 11.7 g) and bis(chloroacetoxy)dimethylsilane (50 mmol, 15.7 g) were dissolved in THF (40 ml) and cooled to 0° C. The suspension of diisopropylamidomagnesium chloride previously prepared was then added dropwise at such a rate that the temperature did not exceed 30° C. The yellow suspension obtained was heated for 30 min to reflux, then cooled, and the brown solution added dropwise to 20% hydrochloric acid (85 ml). The phases were separated and the organic phase concentrated. The residue was recrystallized from isopropanol. 9.56 g (78%) of slightly yellowish crystals were obtained (purity 99.7% by HPLC), m.p. 91–94° C., $^1$H NMR (CDCl$_3$): δ2.95–3.15 (m, 2H, PhCH$_2$CH(NHZ)CO), 3.95 (d, 1H, CHHCl), 4.15 (d, 1H, CHHCl), 4.70–4.80 (m, 1H, CH$_2$CH(NHZ)CO), 5.05 (s, 2H, PhCH$_2$O), 5.20–5.35 (bs, 1H, NHZ), 7.10–7.20 (m, 2H, aromat.), 7.25–7.40 (m, 8H, aromat.).

EXAMPLE 4

Methylmagnesium chloride solution (20% in THF, 100 mmol, 39 ml) was initially charged, heated to boiling and admixed dropwise with diisopropylamine (100 mmol, 14.0 ml). After the addition, the mixture was refluxed for a further 1 h, then cooled.

Methyl benzoate (17 mmol, 2.30 g) and bis (chloroacetoxy)dimethylsilane (17 mmol, 5.33 g) were dissolved in THF (20 ml) and cooled to +5° C. The suspension of diisopropylamidomagnesium chloride previously prepared was then added dropwise at such a rate that the temperature did not exceed 30° C. The suspension obtained was heated for 60 min to reflux. This was then cooled and the brown solution added dropwise to 20% hydrochloric acid (40 ml). The phases were separated and the organic phase concentrated. The residue was analyzed by HPLC. 89.4% of product and 6.3% of reactant were found by retention time comparison with commercial phenacyl chloride. The remainder is unidentified.

EXAMPLE 5

Methylmagnesium chloride solution (20% in THF, 300 mmol, 116 ml) was initially charged, heated to boiling and admixed dropwise with diisopropylamine (300 mmol, 42.0 ml). After the addition, the mixture was refluxed for a further 1 h, then cooled.

Sodium chloroacetate (100 mmol, 11.6 g) and dichlorodimethylsilane (50 mmol, 6.1 ml) were heated in absolute THF (50 ml) to 40° C. for 2 h. Methyl pivalate (50 mmol, 6.70 ml) were added and the reaction mixture cooled to +5° C. The suspension of diisopropylamidomagnesium chloride prepared was then added dropwise at such a rate that the temperature did not exceed 30° C.

The suspension obtained was heated for 60 min to reflux. This was then cooled and the brown solution added dropwise to 12% hydrochloric acid (100 ml). The phases were separated and the organic phase analyzed by GC. 1-Chloro-3,3-dimethyl-2-butanone content 91.2%, reactants content 4.3%. The solvent was distilled off via a column and the residue fractionally distilled. 5.10 g (76%) of main fraction were obtained (GC>95%), b.p. 75–80° C./18 mbar, $^1$H NMR (CDCl$_3$): δ1.20 (s, 9H, tBu), 4.40 (s, 2H, COCH$_2$Cl).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing an α-haloketone of the formula (1)

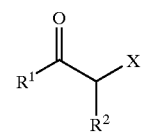

(1)

where $R^1$ is an alkyl, aralkyl or aryl radical in which CH$_2$ units may be replaced by heteroatoms such as NH, NCH$_3$, S or O and CH units may be replaced by N, the $R^1$ radicals optionally substituted by non-interfering functional groups, and $R^2$ is a hydrogen, alkyl, aralkyl or aryl radical, and X is a halogen radical;

by reacting a carboxylic acid derivative of the formula (2)

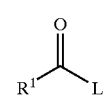

(2)

where $R^1$ is as defined above and

L is a leaving group, with a mono- or dienolate of a silyl ester of the formula (3)

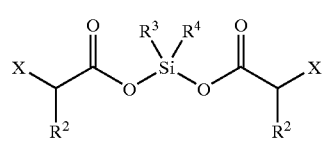

(3)

where $R^3$ and $R^4$ are identical or different alkyl, aryl, alkenyl or aralkyl radicals;

and hydrolyzing the reaction product immediately afterwards by adding acid and decarboxylating to (1).

2. The process of claim 1 wherein said non-interfering functional groups are selected from the group consisting of halogen radicals, amino radicals, alkoxy radicals or thioalkyl radicals.

3. The process of claim 1, wherein said α-haloketone has the formula (5)

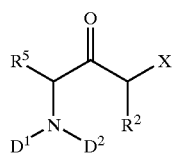
(5)

where $R^5$ is a hydrogen, alkyl, aralkyl or aryl radical in which one or more $CH_2$ groups may be replaced by O, S, NH or $NCH_3$,
X is a halogen radical, and
$D^1$ and $D^2$ are independently a hydrogen radical, an amino protecting group, or together comprise a cyclic amino protecting group, wherein the compound of formula (5) is prepared by reacting an amino acid derivative of the general formula (6)

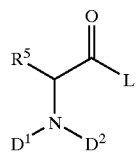
(6)

where L is a leaving group,
with a metal mono- or dienolate of a silyl ester of the general formula (3) and hydrolyzing the reaction product immediately afterwards by adding acid and decarboxylating to (5).

4. The process of claim 1, which is carried out at a temperature in the range of from −10° C. to 110° C.

5. The process of claim 1, which is carried out at a temperature in the range of from 0° C. to 70° C.

6. The process of claim 1, wherein a base is used to generate the enolate of the silyl ester, said base comprising a magnesium amide or a combination of an alkyl magnesium compound with an amine.

7. The process of claim 6, wherein the molar ratio of base to silyl ester is from 2 to 8.

8. The process of claim 6, wherein the molar ratio of base to silyl ester is from 2 to 6.

9. The process of claim 1, wherein the molar ratio of the silyl ester to the carboxylic acid derivative is from 0.5 to 2.

10. The process of claim 1, wherein the molar ratio of the silyl ester to the carboxylic acid derivative is from 0.5 to 1.5.

11. The process of claim 3, wherein the amino acid derivative (6) is an optically active, enantiomerically pure L- or D-amino acid ester.

12. The process of claim 11, wherein the optically active, enantiomerically pure L- or D-amino acid ester comprises a tert-butoxycarbonyl- or benzyloxycarbonyl-protected L-phenylalanine ester or a butoxycarbonyl- or benzyloxycarbonyl-protected L-S-phenylcysteine ester.

13. A process for preparing an α-haloalcohol of the general formula (4)

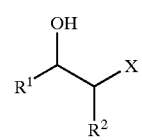
(4)

comprising preparing an α-haloketone (1) by the process of claim 1, and reducing the α-haloketone (1) to the α-haloalcohol (4).

14. A process for preparing an α-haloalcohol of the general formula (7)

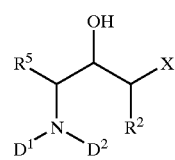
(7)

comprising preparing an α-haloketone (5) by the process of claim 3, and reducing the α-haloketone (5) to the secondary alcohol (7).

* * * * *